United States Patent
Kööbi et al.

(10) Patent No.: US 6,228,033 B1
(45) Date of Patent: May 8, 2001

(54) APPARATUSES AND METHODS FOR A NONINVASIVE MEASUREMENT OF PHYSIOLOGICAL PARAMETERS

(75) Inventors: Tiit Kööbi, Halmeenkatu 6 F, Fin-33700, Tampere (FI); Ants Aher, Graniidi 29-16, Tallin; Jürgen Lamp, Vindi Tee 4, Saku Vald, both of (EE), 75501

(73) Assignees: Tiit Koobi; Ants Aher; Jurgen Lamp; Heiki Silem

( * ) Notice: Subject to any disclaimer, the term of this patent is extended or adjusted under 35 U.S.C. 154(b) by 0 days.

(21) Appl. No.: 09/423,879
(22) PCT Filed: May 13, 1998
(86) PCT No.: PCT/FI98/00409
§ 371 Date: Nov. 15, 1999
§ 102(e) Date: Nov. 15, 1999
(87) PCT Pub. No.: WO98/51211
PCT Pub. Date: Nov. 19, 1998

(30) Foreign Application Priority Data

May 14, 1997 (FI) .................................................. 972067

(51) Int. Cl.[7] ................................................... A61B 5/02
(52) U.S. Cl. .................... 600/483; 600/485; 600/529; 600/547
(58) Field of Search ...................... 600/481, 483–488, 600/490, 500, 504–506, 513, 529, 531–538, 547

(56) References Cited

U.S. PATENT DOCUMENTS

| | | |
|---|---|---|
| 3,996,925 | 12/1976 | Djordjevich . |
| 4,562,843 | 1/1986 | Djordjevich et al. . |
| 4,860,759 | 8/1989 | Kahn et al. . |
| 5,343,867 | 9/1994 | Shankar . |
| 5,467,768 | 11/1995 | Suda et al. . |
| 5,469,859 | * 11/1995 | Tsoglin et al. ........................ 600/536 |
| 5,782,774 | * 7/1998 | Shmulewitz ..................... 600/547 X |

FOREIGN PATENT DOCUMENTS

| | | |
|---|---|---|
| 0 575 984 | 12/1993 | (EP) . |
| WO 90/00367 | 1/1990 | (WO) . |
| WO 94/10902 | 5/1994 | (WO) . |

* cited by examiner

*Primary Examiner*—Cary O'Connor
*Assistant Examiner*—Ryan Carter
(74) *Attorney, Agent, or Firm*—Young & Thompson (57) ABSTRACT

The present invention relates to apparatuses and methods for measuring three important physiological systems, circulation, breathing, and body water compartments. More specifically, the present invention relates to apparatuses and methods for a continuous simultaneous/synchronized and noninvasive measurement of heart pump function, elastic properties of the vascular system, systemic vascular resistance, breathing capacity, and body water compartments through the combined use of bioimpedance and continuous blood pressure measurement techniques (5, 6) and, optionally, spirometry (7) and/or plethysmography.

9 Claims, 2 Drawing Sheets

APPARATUSES AND METHODS FOR A NONINVASIVE MEASUREMENT OF PHYSIOLOGICAL PARAMETERS

BACKGROUND OF THE INVENTION

The present invention relates to apparatuses and methods for measuring three important physiological systems, circulation, breathing, and body water compartments. More specifically, the present invention relates to apparatuses and methods for a continuous simultaneous/synchronized and noninvasive measurement of heart pump function, elastic properties of the vascular system, systemic vascular resistance, breathing capacity, and body water compartments through the combined use of bioimpedance and continuous blood pressure measurement techniques and, optionally, spirometry and/or plethysmography.

The monitoring of the cardiovascular system and breathing is of major importance in the treatment and follow-up of critically ill patients, in the diagnosis of various disorders in the blood circulation and in the assessment and follow-up of medication of patients suffering from hypertension or cardiac malfunction. Typical parameters that reflect the status of cardiovascular and respiratory systems and are to be monitored are stroke volume, breathing related changes of the stroke volume, cardiac output, heart rate, arterial compliance, peripheral vascular resistance, breathing rate, breathing amplitude (tidal volume), and blood pressure. The monitoring of the cardiovascular parameters may also find use in scientific research and sports medicine. Cardiovascular system is inherently a multivariate closed-loop system. Main parameters of the system have a close mutual interrelation mediated by various mechanical and neural mechanisms. The autonomous nervous system controls different parts of this system by a continuous neural modulation causing small variations of the variables around their mean values. The breathing as an external stimulator modulates the hemodynamic parameters significantly. The relationship and interaction between the circulation and breathing is very tight, which emphasizes the need of simultaneous estimation of these systems in clinical work.

Body fluids play an important role in body homeostasis. The extracellular water retention is common in renal insufficiency and is also noted in cardiac insufficiency. Exaggerated dehydration may occur as a side-effect in treatment with diuretics, for example in patients with hypertension. Thus the simultaneous evaluation of the body water compartments would add essentially to a comprehensive and accurate evaluation of a patient's status.

At present the functional state of cardiovascular system and its coherence with respiration, vascular properties, and body fluids have been studied with separate measuring methods and devices at different stages. The combination of separate methods does not offer a reliable basis for the overall estimation of the patient's status, since the correlation of the results is inadequate and far from optimum. An establishment of the closed-loop interactions between different variables and a quantitative determination of cardiovascular parameters are not possible.

Only invasive methods have been considered reliable to measure the most important parameter of the heart pump function, the stroke volume, and its derivative, cardiac output (the blood volume pumped by the heart in one minute). The use of invasive methods in cardiac output measurement is expensive and is mostly restricted to critically ill patients. These methods involve a complication risk to the patient, e.g., catheter sepsis, bleeding, pneumothorax, and even death. There are nevertheless other patient groups who require hemodynamic evaluation, such as the patients with chronic heart failure, syncope, arterial hypertension, hemodialysis, etc.

Several approaches have been made to find an alternative to the invasive methods. An ideal method for the measurement of the cardiac output would be noninvasive and continuous. The impedance cardiography has both these features and has been an object of intensive research during the last 30 years. Noninvasive thoracic impedance methods for the measurement of the stroke volume originally described by Kubicek, W. G. et al. [Aerospace Med. 37 (1966) 1208–1212] have been evaluated extensively. However, the level of agreement with the invasive methods has varied widely indicating the imprecision of the thoracic methods [Fuller, H. D., Clin. Invest. Med. 15 (1992) 103–112; Mehisen, J. et al., Clin. Physiol. 11 (1991) 579–588; Pickett, B. R. and Buell, J. C., Am. J. Cardiol. 69 (1992) 1354–1358; Yakimets, J. and Jensen, L., Heart Lung 24 (1995) 194–206; Atallah, M. M. and Demain, A. T., J. Clin. Anaesthesia 7 (1995) 182–185]. Furthermore, the thoracic impedance methods provide information only about a limited number of cardiovascular parameters, no information can be obtained, eg., about the whole body water compartments or different peripheral pulsatile parameters.

Based on the use of a thoracic bioimpedance measurement, U.S. Pat. No. 4,807,638 discloses a method and a device for a noninvasive continuous monitoring of mean arterial blood pressure and certain cardiac parameters, namely cardiac index, left cardiac work index and systemic vascular resistance index. However, it is well known in the art that a blood pressure measurement based on impedance is not reliable.

In the 1970s Tishchenko developed an alternative impedance method, the whole-body impedance cardiography known also as integral rheography and integral impedance plethysmography [Tishchenko, M. I., Sechenov Physiol. J. 59 (1973) 1216–1224; Tishchenko, M. I., et al., Kardiologiia 13(11) (1973) 54–62]. The whole-body impedance cardiography differs from thoracic impedance methods in its placement of electrodes, the lower frequency of the alternating current used, and the stroke volume equation. Even though the whole-body impedance cardiography has shown excellent agreement with the thermodilution, which currently is the most widely used invasive method for the measurement of cardiac output [T. Kööbi et al., Medical & Biological Engineering & Computing 34, Suppl. 1, Part 2, (1996) 163–164 (Proceedings of the 1st International Conference on Bioelectromagnetism. Jun. 9–13, 1996, Tampere, Finland)], it alone cannot provide sufficient data to allow a reliable overall assessment of cardiorespiratory condition of the patient.

The need for a simple and noninvasive diagnostic apparatus and methods for simultaneous measurement of cardiorespiratory status is evident.

The object of the present invention is to provide an apparatus and a method for a continuous, simultaneous/synchronized noninvasive measurement of cardiorespiratory and related parameters.

Another object of the present invention is to provide a apparatus and a method for a continuous, simultaneous/synchronized noninvasive measurement of cardiorespiratory and related parameters producing reliable, quantitative data for the establishment of the patients status on a real-time basis.

Yet another object of the present invention is to provide an apparatus and a method for a continuous, simultaneous/ synchronized noninvasive measurement of cardiorespiratory and related parameters providing common basis for a reliable determination of the patient's status.

Yet another object of the present invention is to provide an apparatus and a method for a continuous, simultaneous/synchronized noninvasive measurement of cardiorespiratory and related parameters enabling a simple manipulation of the patient at a time without causing stress to the patient.

Yet another object of the present invention is to provide an apparatus and a method for a continuous, simultaneous/synchronized noninvasive measurement of cardiorespiratory and related parameters based on a simultaneous/synchronized noninvasive measurement of bioimpedance in the whole body and body segments on heartbeat-to-heartbeat basis and the blood pressure and, optionally, spirometry and/or plethysmography.

SUMMARY OF THE INVENTION

The apparatuses and the methods of the present invention meet the above objects and overcome the drawbacks of the prior art. The apparatuses and the methods of the present invention are characterized by what is stated in the claims. The present invention provides an apparatus for a continuous simultaneous/synchronized noninvasive measurement of heart pump function, elastic properties of the vascular system, systemic vascular resistance, breathing capacity, and extracellular and intracellular body water compartments. The measurement is simple to perform and does not stress the patient, since the information necessary to evaluate the cardiorespiratory status of the patient is obtained at a time and using the same electrode connections. The respiratory parameters obtained by the impedance technique may easily be supplemented, if desired, with more precise by a spirometric measurement using a flow sensor attachable to the patient. Similarly, if a more precise estimation of the status of blood vessels on extremities is wished, using cuffs which close the arterial or venous blood flow, classical venous occlusion plethysmograms can be obtained. Synchronizing the blood pressure, cardiac output and plethysmographic information enables a reliable and precise estimation of the status of blood vessels on extremities. The results of the simultaneous blood pressure measurements enable the precise calculation of more parameters than with known noninvasive methods.

The apparatus of the present invention is useful for the follow-up of the heart performance in normal laboratory diagnostics and in the intensive care. Since it is now possible to measure several hemodynamic parameters at the same time, it is possible to obtain data concerning the patient's condition and treatment continuously on real-time basis. Furthermore, the patient can be connected to the apparatus even using conventional ECG-electrodes thus making the measurement considerably easier and less dangerous for the patient compared with the measurement using invasive methods. Also the costs of the equipment are less than those of known methods.

The apparatus of the invention makes use of the impedance principle of the conventional whole body impedance cardiography supplemented by simultaneous pulse wave velocity measurement and blood pressure measurement using a pressure sensor, and optionally spirometry and/or plethysmography.

The apparatus of the invention comprises a bioimpedance device which is electrically connectable to the distal parts of the arms and legs of the patient through a first set of electrodes comprising at least one current injecting electrode for a leg and one for an arm and at least one voltage sensing electrode for a leg and one for an arm. Preferably a pair of both current injecting electrodes and voltage sensing electrodes are used. Since nearly the whole body is connected between the electrodes, the bioimpedance device of the invention injects the current and senses the pulsatile variations in the whole body. The high-frequency constant alternating current of 10–100 kHz and 0.1–10 mA is injected via an injecting output (channel). The frequency used is preferably 30–70 kHz, the frequency of 30 kHz being most preferred. The constant high frequency alternating current used is preferably 0.5–4 mA, the current of 0.7 mA being most preferred. The flow of current through the electrical impedance of the tissues and the fluids of the body generates a voltage that is sensed by voltage sensing electrodes. The amplitude of the heart synchronous bioimpedance variation is proportionally related to the left ventricular stroke volume.

From these same electrodes attachable to the distal parts of the arms and legs of the patient, the basal impedance of the body is measured using different current frequencies, and whole-body water compartments are calculated from this basal impedance. The current frequencies used can vary between 1 kHz–1 MHz. For the extracellular water estimation the preferred range is 1–100 kHz, the range of 10–30 kHz being most preferred, and for the total body water estimation the preferred range is 100 kHz–1 MHz, preferably 100–500 kHz. Breathing related slow frequency variations of the basal impedance are used to calculate the breathing frequency, and from the amplitude of these variations an estimate of the breathing volume is calculated. If more accurate data concerning the breathing function are wished, an additional flow sensor can be used. The electrocardiographic (ECG) data is also obtained via the voltage sensing electrodes or, optionally, from additional chest electrodes.

The apparatus further includes one or more voltage sensing inputs (channels) which are attachable to the different body segments through a second set of electrodes comprising at least one pair of electrodes to sense the pulsatile changes of voltage and to calculate the impedance in body segments caused by the same above mentioned injected current. The time interval between the whole-body heartbeat related impedance variation obtained through the first set of electrodes and the distal segment impedance variation obtained through the second set of electrodes is proportional to distance between the heart and said segment, and inversely related to the arterial compliance of the patient. The amplitude of the segmental heartbeat related impedance changes is proportional to the blood flow in these segments reflecting the condition of the arteries proximal from the segment.

The set of electrodes positionable on the patient to inject the output of the current source into the patient and to sense and mediate the voltage alterations to the input of the current source can be, eg., standard spot, pre-gelled disposable ECG electrodes.

The bioimpedance device has a current source having at least one output capable of injecting a desired predetermined current with desired predetermined different fixed frequencies.

The bioimpedance device of the invention further includes an electronic circuit connectable to the voltage sensing inputs and the electrodes positionable on different segments of the patient's body to sense the voltage caused by current flow through the segments of the body and to generate output signals. The magnitude of the output signal changes is in accordance with the pulsatile blood flow in the whole body and in body segments. A blood pressure sensor has also a connection to the electronic circuit of the bioimpedance device of the present invention to simultaneously measure the blood pressure of the patient. If a respiratory flow sensor is used, it is also connected to the electronic circuit of the bioimpedance device of the invention. Furthermore, if segmental plethysmograms are wished to be recorded, i.e. the estimation of the status of blood vessels on extremities is wished, a conventional occlusion plethysmographic measurement can be used.

The apparatus of the invention further contains a computational circuit block. The electrical circuit of the bioimpedance device receives the sensed voltages, amplifies them and filters out the high frequency components. The whole-body basal impedance ($Z_o$), the change in whole-body and optional additional impedance signals (dZ), the ECG, the blood pressure, and, optionally, the spirometer signals and/ or plethysmographic signals are digitized and directed to a computational circuit block. All signals are displayed on the display with the on-line processed measurement results.

The present invention further includes a method for simultaneously/synchronously noninvasively measuring various cardiorespiratory and related parameter by means of the apparatus of the invention. The method comprises the steps of electrically connecting a bioimpedance device to the distal parts of the arms and legs of a patient through a first set of electrodes comprising at least one current injecting electrode for a leg and one for an arm and at least one voltage sensing electrode for a leg and one for an arm, for injecting a first high-frequency constant alternating current and sensing the pulsatile heart related voltage variations in the whole body resulting from the electrical impedance of the tissues and the fluids in the whole body and for obtaining electrocardiographic signals from the heart (ECG) and, alternating with said first current, for injecting high-frequency constant alternating currents of predetermined, different fixed frequencies and sensing different voltages caused by the different high-frequency currents in the body, electrically connecting the bioimpedance device to different body segments of the patient through a second set of electrodes comprising at least one pair of sensing electrodes for sensing the pulsatile heart related voltage changes in said segments caused by said first injected current in body segments, electrically connecting a pressure sensor to a suitable location on the patient for measuring the blood pressure, and thereafter amplifying and digitizing the voltages sensed by said first sensing electrodes and the changes in voltages sensed by said second sensing electrodes and the signals obtained from the pressure sensor, transmitting the digitized data to a computational circuit block for calculating the desired cardiorespiratory and related parameter, such as the stroke volume, the stroke index, the breathing related changes of the stroke volume, the stroke volume distribution index, the heart rate, the cardiac output, the cardiac index, the pulse wave velocity/arterial compliance, the breathing frequency and amplitude, and the body water compartments, and furthermore, with the blood pressure data available, for calculating the systolic arterial pressure, the diastolic arterial pressure, the mean arterial pressure, the systemic vascular resistance, the systemic vascular resistance index, the left cardiac work, the left cardiac work index, and the arterial compliance, and displaying the calculated data on a display with the on-line processed measurement results.

In a preferred embodiment, the method of the present invention further comprises a step of electrically connecting a respiratory flow sensor to the patient's mouth/nose for measuring the patient's respiration continuously.

In a second preferred embodiment, the method of the present invention further comprises a step of performing a conventional occlusion plethysmography measurement in segments of the extremities of a patient, wherein at least a pair of cuffs is used to close the arterial or venous blood flow in said segment of the patient, e.g. in a leg. A pressure higher than the arterial pressure is applied to the lower cuff essentially occluding the flow of blood. A pressure of about 30–60 mmHg is applied to the upper cuff occluding the venous flow of the blood. The arterial flow to the segment between the cuffs continues and results in the filling of the veins and tissues with blood. Consequently, the basal impedance of the segment between the voltage sensing electrodes decreases. The rate of the impedance decrease is directly related to the arterial flow in the leg. When the upper cuff is deflated, the resulting impedance change/increase is characteristic to the venous capacitance.

BRIEF DESCRIPTION OF THE DRAWINGS

The invention will now be described by way of examples in more detail with reference to the accompanying drawings, in which.

DETAILED DESCRIPTION OF THE INVENTION

Figure 1:
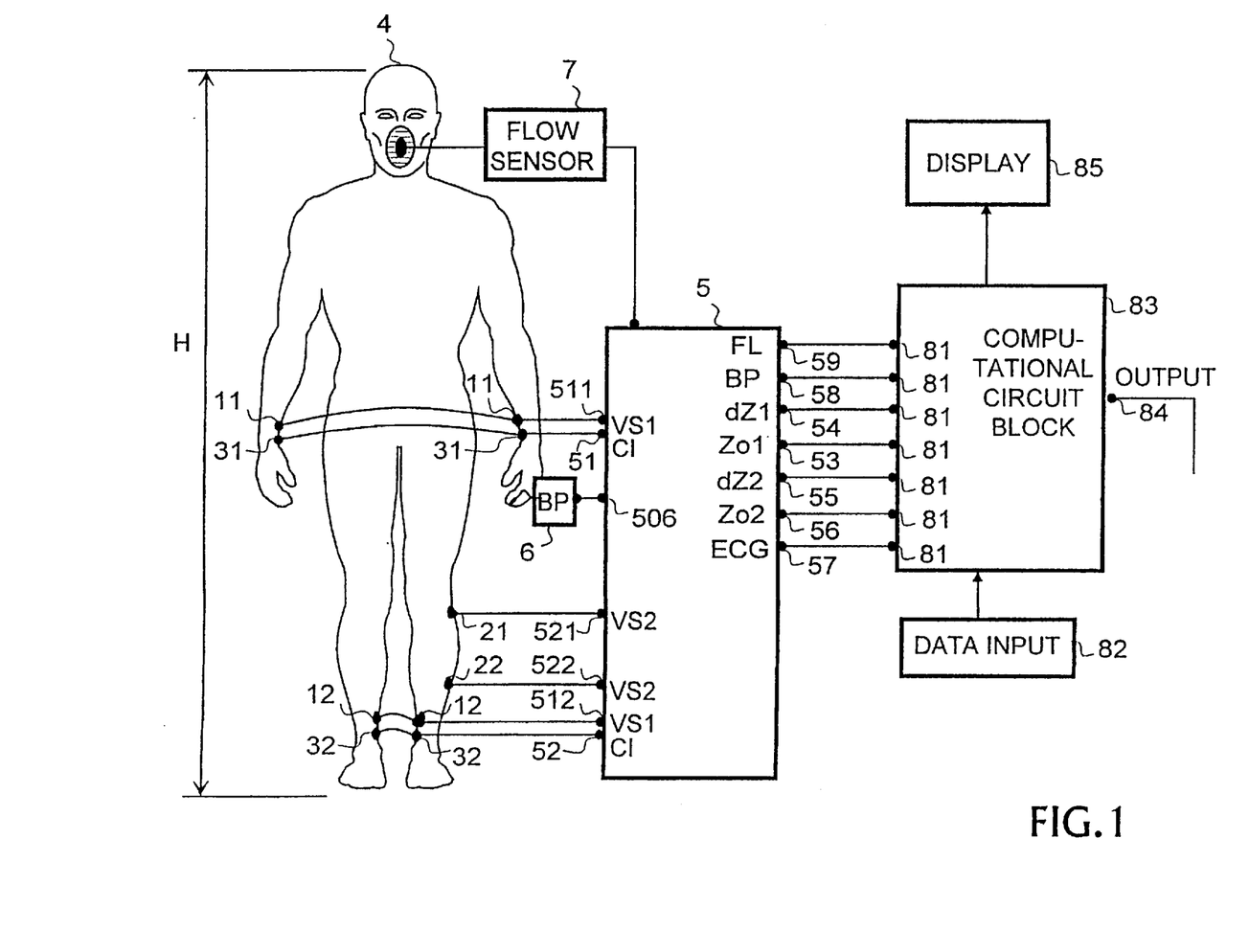
FIG. 1 is a block diagram that illustrates the first preferred embodiment of the apparatus interconnected with the patient.

FIG. 1 illustrates the use of an especially preferred embodiment of an apparatus constructed in accordance with the present invention showing the interconnections to a patient 4.

The apparatus comprises current injecting electrodes for injecting current into patient's body and voltage sensing electrodes for sensing the voltage generated by the current flowing through the patient's tissues and fluids.

A pair of first current injecting electrodes 31 is shown attached to the wrist areas of the patient, advantageously to the inner side of wrist, one electrode to each wrist area. A pair of second current injecting electrodes 32 is attached to the ankle areas of patient, advantageously to the inner side of ankle, one electrode to each ankle area. The first current injecting electrodes 31 and the second current injecting electrodes 32 delineate a first outer body segment that includes the tissues and fluids of the body between the four electrodes 31 and 32, that is to say the tissues and fluids of nearly the whole body. A pair of first voltage sensing electrodes 11 is attached to the arm areas of the patent, one electrode to each arm area proximally from the current injecting electrode 31, advantageously about 5 cm from the current injecting electrode 31. A pair of second voltage sensing electrodes 12 is attached to the calf areas of patient, one electrode to each calf area proximally from the second current injecting electrode 32, advantageously about 5 cm from the current injecting electrode 32. The first voltage sensing electrodes 11 and the second voltage sensing electrodes 12 delineate a first inner body segment that includes the tissues and fluids of the body between the four electrodes 11 and 12, that is to say the tissues and fluids of nearly the whole body. The first inner body segment is advantageously included within the first outer body segment. Each pair of electrodes are symmetrically disposed about the frontal centerline of the patient 4.

It should be understood that although pairs of electrodes 11, 12, 31, and 32 are shown, in many applications single electrodes can be used instead. Then the measurements are concentrated only on half body and the results are less accurate.

The apparatus comprises also voltage sensing electrodes 21 and 22 for sensing pulsatile changes. A third voltage sensing electrode 21 is shown to be attached to the upper part of a patient's calf, advantageously to the outer side of the calf. A fourth voltage sensing electrode 22 is shown to be attached to the lower part of the same calf, advantageously to the outer side of the calf. The third and the fourth sensing electrodes 21 and 22 can be attached to other areas of the patient 4 as long as the area is within the first outer body segment. They delineate a second body segment that includes the tissues and fluids of the body between the two electrodes 21 and 22. The second inner body segment is included within the first outer body segment.

Although not shown in the FIG. 1 the apparatus can also comprise other voltage sensing electrodes, which delineate body segments and are attached to the patient within the first outer body segment.

The electrodes 11, 12, 21, 22, 31 and 32 are advantageously standard spot, pre-gelled disposable ECG electrodes. Also other standard electrodes, such as band electrodes, can be used. The positioning of electrodes is not critical and can vary from what is explained and shown in the picture.

The apparatus also comprises a bioimpedance measuring device 5 for measuring the impedance changes and ECG. The pair of first voltage sensing electrodes 11 and the pair of second voltage sensing electrodes 12 are electrically connected to a first voltage sensing input 511 and a second voltage input 512, respectively, of a bioimpedance measuring device 5. The pair of first current injecting electrodes 31 and the second current injecting electrodes 32 are electrically connected to a first and second current injecting output 51 and 52, respectively, of the bioimpedance measuring device 5. In like manner, the third voltage sensing electrode 21 and the fourth voltage sensing electrode are electrically connected to a third voltage sensing input 521 and a fourth voltage sensing input 522, respectively, of the bioimpedance measuring device 5. If other voltage sensing electrodes are used, they are electrically connected to corresponding inputs of the bioimpedance measuring device 5.

The bioimpedance measuring device 5 is a microprocessor controlled noninvasive continuous measuring device, that comprises at least two pairs of inputs, namely a first voltage sensing pair VS1 of inputs 511 and 512 and a second voltage sensing pair VS2 of inputs 521 and 522, at least one current injecting pair CI of outputs 51 and 52, a current source (not shown in the picture) for generating a high-frequency, advantageously constant amplitude, alternating current with different predetermined frequencies, at least one analog-to-digital converter (not shown in the picture) for changing the measured analog signals to digital signals and at least one electrical circuit (not shown in the picture) for generating outputs used as inputs of a computational circuit block 8. The first voltage sensing pair VS1 of inputs is called also a first channel, the second voltage sensing pair VS2 of inputs is called also a second channel and the current injecting pair CI of outputs is called also a third channel. The analog-to-digital converter can for example have 7 channels with 12 bits in each channel with sampling rate 200 Hz. The electrical circuit can be included as a part of the analog-to-digital converter. The current source changes the current frequencies in a predetermined manner which can be pre-programmed into the current source or current source can get orders from the computational circuitry or via the keyboard (the last two are explained later). By using different current frequencies the body water compartments can be measured.

In the first preferred embodiment a blood pressure sensor 6 is connected to the apparatus as shown in the FIG. 1, where the blood pressure sensor 6 is attached to the finger of patient 4 and is electrically connected to a fifth input 505 of the bioimpedance measuring device 5 for measuring blood pressure continuously. Different kind of commercially available blood pressure measuring devices can be used and the blood pressure can be measured also from other parts of the patient. Also a respiratory flow sensor 7 is connected to the apparatus in the first preferred embodiment as shown in the FIG. 1, where the respiratory flow sensor 7 is attached to patient's 4 mouth/nose and is electrically connected to the sixth input 506 of the bioimpedance measuring device 5 for measuring the patient's respiration continuously.

It should be understood that in other embodiments the blood pressure sensor 6 and/or the respiratory flow sensor 7 may not be needed and therefore may not be connected to the apparatus.

The bioimpedance measuring device 5 also provides digitized ECG values to output 57 from the inputs of the voltage sensing electrodes 11, 12, 21 and 22.

If a blood pressure sensor 6 and/or a respiratory flow sensor 7 is connected to the bioimpedance measuring device 5, it amplifies the detected signals and provides digitized outputs BP and FL to outputs 58 and 59, respectively.

It should be understood that the number of outputs and inputs in bioimpedance measuring device can vary from what is shown in the FIG. 1.

By connecting current injecting outputs 51, 52 and all the inputs 511, 512, 521, 522, 506 and 507 to only one measuring device 5 all the measured values can be synchronized and used together for analyzing the patient.

The apparatus also comprises means for analyzing measured data, for example a computer, which comprises various signal inputs 81 and data inputs 82, a computational circuit block 83, at least one output 84 and a display 85. Data input can be for example a keyboard or a disk drive. The number of inputs and outputs can vary from what is shown in the picture. The bioimpedance measuring device can be included as a part of this computer.

The basal impedance of the first inner body segment Zo1 (that means in this embodiment the whole body basal impedance), the change in the basal impedance of the first inner body segment dZ1 (that means in this embodiment the change in the whole body basal impedance), the basal impedance of the second inner body segment Zo2, the change in the basal impedance of the second inner body segment dZ2, the ECG value and other possible digitized signals are provided as inputs to the computational circuitry represented by the computational circuit block 83. It is programmed to process the values to different parameters, for example:

stroke volume is calculated on the basis of the first whole body basal impedance Zo1 (that is the basal impedance of the first inner body segment) and the pulsatile changes in the first whole body basal impedance dz with one current frequency;

body water compartments are calculated on the basis of the first whole body basal impedance Zoa with at least two different current frequencies;

the pulse wave velocity is calculated on the basis of the time interval between the change in the first whole body basal impedance dz and the second whole body basal impedance dz of the body segments;

mean arterial blood pressure is calculated on the basis of blood pressure B;

breathing frequency and breathing amplitude are calculated on the basis of FL or the first whole body basal impedance Zoa.

With the help of these parameters and measured and/or values given through the data input 82 (for example patient's 4 height H given via the keyboard) various parameters can be calculated as described later. The results can be shown in the display 85 or printed via the output 84.

The following equations and relationships can be used for the calculation of different parameters.

The stroke volume (S) is the volume of blood the left ventricle ejects per each contraction of the heart. The stroke volume is calculated on the basis of whole-body impedance cardiography stroke volume equation with current injecting and sensing electrodes on the wrists and ankles. It is directly proportional to the amplitude of the heart synchronous impedance variation dZ. The S equation is the following:

$$S = k \times dZ/Z \times H^2 \times C/D/Z \quad (1)$$

Wherein H is height (cm); dZ is the amplitude of heart synchronous impedance variation of the whole body (in ohms); Z is the calibration factor (0.1 ohms); Z is baseline impedance of the whole body (in ohms); C is the duration of the cardiac cycle; and D is the duration from the largest deflection of the heart synchronous impedance variation to the onset of the next cycle. Coefficient k is derived from blood resistivity, the relation between the distance of the voltage electrodes and body height, and it also includes a correction by the patient's body mass index and haematocrit.

The stroke volume index (S; m/m$^2$) is the stroke volume normalized by body surface area (S=S/BSA) and is typically used to compare the S of different size individuals. The BSA is calculated using the equation:

$$BSA = H^{0.425} \times W^{0.725} \times 0.007184$$

wherein H is height (cm) and W is weight (kg).

The heart rate (HR, 1/min) is obtained from the ECG signal.

The cardiac output (CO) is calculated from the equation:

$$CO = S \times HR$$

The cardiac index (CI, 1/min/m$^2$) is the body surface area normalized cardiac output (CI=CO/BSA) and is typically used to compare the CO of different size individuals.

The stroke volume distribution index (SVDI, %) is calculated from the equation:

$$SVDI = 100 \times C/D$$

SVDI (%) characterizes the S distribution between the central and peripheral parts of the circulation. The higher the value the smaller part of the S is arriving to the periphery. This parameter depends mainly on the arterial tone.

The pulse wave velocity (PWV) in arterial system depends on the arterial compliance. The higher the compliance, the lower the PWV and vice versa. It means that the PWV can be applied for indirect estimation of the arterial compliance.

PWV measurements are based on the principle that the speed of propagation of a pressure pulse in a fluid-filled elastic tube depends on the elastic modulus of the tube material as well as on the lumen radius to wall thickness ratio. The stiffer the tube the higher the speed of pulse wave propagation. By measuring the speed of propagation it is therefore possible to determine an index of the average elastic state of the vessel pathway. Pressure pulse and flow pulse propagate with the same velocity. Measuring the pulsatile impedance changes at two points in the arterial system it is possible the average PWV down that arterial segment to be calculated.

The time delay designated as pulse transit time (PTT) is measured between the feet of the whole-body and the distal body segment impedance waves. The foot of the heart related impedance wave is defined as the point of the commencement of a sharp systolic upstroke. The distance traveled by the pulse wave is measured over the surface of the body with a tape measure as the distance between the recording sites.

Average pulse wave velocity can be recorded if the second voltage sensing channel is placed on a distal part of the body, for example on calf. Regional pulse wave velocities can be measured in different segments of the body using simultaneously two voltage sensing channels.

Further parameters that can be obtained are the following:
Systemic vascular resistance (SVR) is calculated from:

$$SVR = 80 \times (MAP - CVP) \times CO$$

wherein MAP is the mean arterial blood pressure and CVP is a central venous pressure (can be measured invasively, default value is 3 mmHg).

Systemic vascular resistance index (SVRI) is calculated from:

$$SVRI = 80 \times (MAP - CVP)/CI$$

wherein MAP, CVP and CI are as defined above.
Left cardiac work (LCW) is calculated from:

$$LCW = 0.0144 \times (MAP - PAOP) \times CO$$

wherein MAP and CO are as defined above and PAOP is pulmonary artery occlusion pressure (can be measured invasively, default value is 6 mmHg).

Left cardiac work index (LCWI) is calculated from:

$$LCWI = 0.0144 \times (MAP - PAOP) \times CI$$

wherein MAP, PAOP and CO are as defined above.

The breathing rate (frequency) and the breathing amplitude/tidal volume are calculated from the body basal impedance fluctuations. The amplitude of the breathing related basal impedance fluctuations (in ohms) is characterizing the breathing volume.

Extracellular, intracellular, and total body water volumes (ECW, ICW, TBW) are calculated from generally accepted relation H$^2$/Z as follows:

$$ECW; TBW = c \times H^2 / Z$$
$$ICW = TBW - ECW$$

wherein H is height (cm), Z is the basal impedance measured at two different frequency ranges (described above) and c is a correction factor derived from the body mass and patient's sex.

Figure 2:
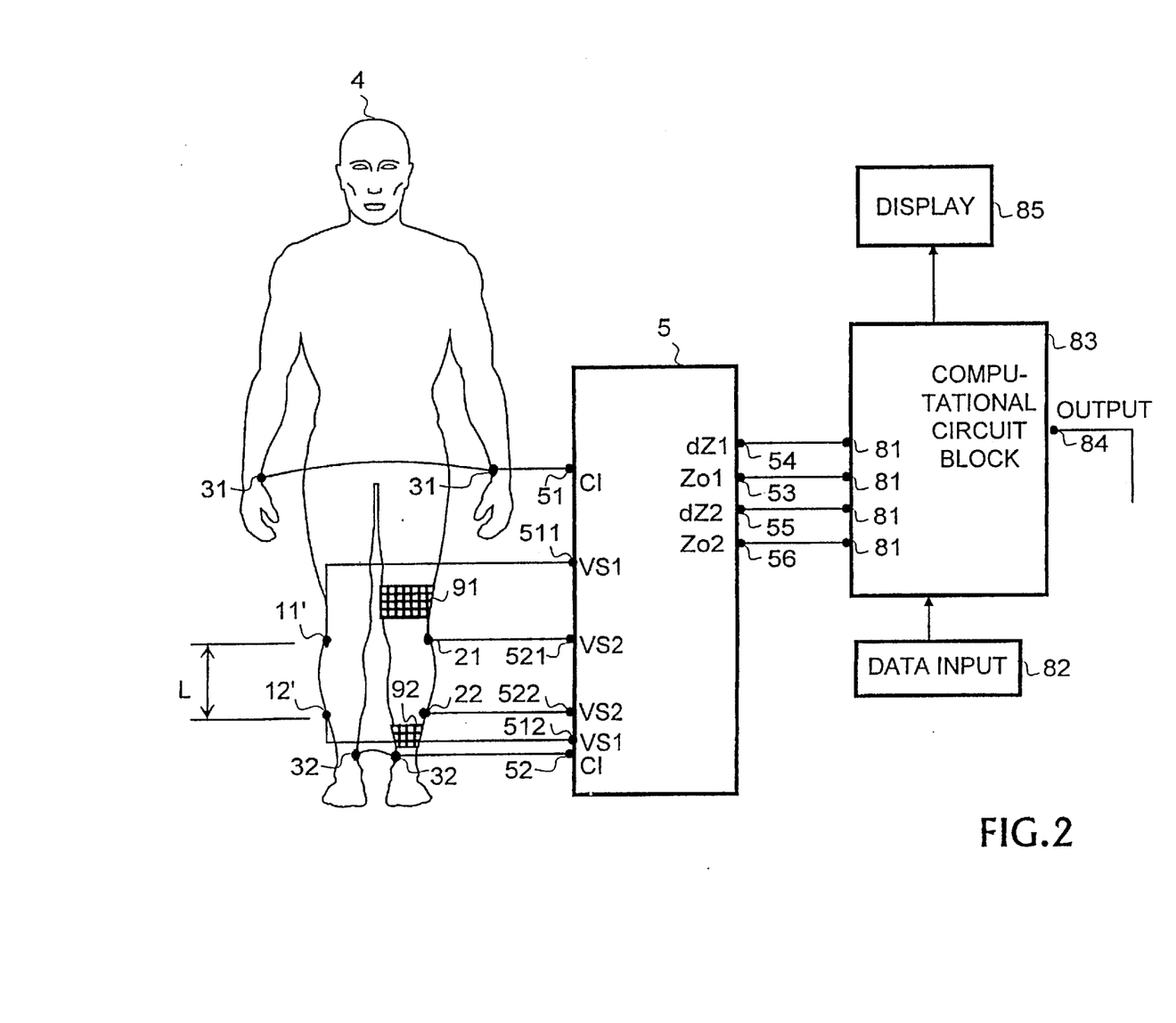
FIG. 2 is a block diagram that illustrates the second preferred embodiment of the apparatus interconnected with the patient.

FIG. 2 illustrates the second preferred embodiment of the apparatus constructed in accordance with the present invention showing the interconnections to a patient 4. The second preferred embodiment is a plethysmography application. With the help of the second preferred embodiment it is shown that various measurements can be done with only one apparatus constructed in accordance with the present invention.

In the second preferred embodiment the bioimpedance measuring device 5 and the means for analysing the measured data (e.g. various signal inputs 81 and data inputs 82, a computational circuit block 83, at least one output 84 and a display 85) are the same as in the first preferred embodiment illustrated in FIG. 1 with the exception that the blood pressure sensor and the respiratory flow sensor are not used and therefore not shown in the picture. It should be understood that these two preferred embodiments can be combined or done one after the other and that various kind of embodiments are possible.

In the second preferred embodiment illustrated in the FIG. 2 the placement and the number of electrodes differs from what is shown in the FIG. 1 with the exception that the current injecting electrodes are attached in the same places. The pair of first current injecting electrodes 31 is shown attached to the wrist areas of the patient, advantageously to the inner side of wrist, one electrode to each wrist area. The pair of second current injecting electrodes 32 is attached to the ankle areas of patient, advantageously to the inner side of ankle, one electrode to each ankle area. The first current injecting electrodes 31 and the second current injecting electrodes 32 delineate a first outer body segment that includes the tissues and fluids of the body between the four electrodes 31 and 32, that is to say the tissues and fluids of nearly the whole body.

The first voltage sensing electrode 11' is shown to be attached to the upper part of the patient's calf, advantageously to the outer side of calf. The second voltage sensing electrode 12' is attached to the lower part of the same calf, advantageously to the outer side of the calf. They delineate a first body segment that includes the tissues and fluids of the body segment between the two electrodes 11' and 12'. The first inner body segment is included within the first outer body segment. The third voltage sensing electrode 21 is shown to be attached to the upper part of the patient's other calf, advantageously to the outer side of calf. The fourth voltage sensing electrode 22 is shown to be attached to the lower part of the patient's other calf, that is to the same calf as electrode 21 and advantageously to the outer side of calf. The distance between the third and the fourth sensing electrode 21 and 22 is the same as the distance L between the first and the second voltage sensing electrode. The electrodes 11' and 21 are advantageously symmetrically disposed about the frontal centerline of the patient 4. In like manner also the electrodes 12' and 22 are advantageously symmetrically disposed about the frontal centerline of the patient. The third and the fourth voltage sensing electrodes 21 and 22 delineate a second body segment that includes the tissues and fluids of the body between them. The second inner body segment is included within the first outer body segment.

By placing electrodes 11', 12', 21 and 22 symmetrically as described earlier the comparison of basal impedance and pulsatile impedance changes on both extremities is possible, because amplitudes are normally equal in both sides.

In the second preferred embodiment cuffs 91 and 92 are used for occluding the vessels of the extremities. The cuffs 91 and 92 are placed first to the other calf and then to the other calf or pairs of cuffs can be used. The cuffs 91 and 92 are placed so that the inner body segment which is to be measured (e.g. the second inner body segment delineated by the third electrode 21 and the fourth electrode 22) is within the area which the cuffs delineate. A pressure higher than the arterial pressure is applied to the lower cuff 92 essentially occluding the flow of blood. A pressure of about 30–60 mmHg is applied to the upper cuff 91 occluding the venous flow of the blood. The arterial flow to the inner body segment between the cuffs 91 and 92 continues and results in the filing of the veins and tissues with blood.

It should be understood that the electrodes 11', 12', 21, 22 and the cuffs 91 and 92 can be placed anywhere in the patient's extremities within the first outer body segment.

Briefly, the bioimpedance measuring device 5 generates a high frequency alternating current that is injected into the patient's body via the current injecting pair CI of outputs 51 and 52 so that it flows through the first outer segment between the pairs of first current injecting electrodes 31 and second injecting electrodes 32. The current flowing through the tissues and fluids of the first outer segment also necessarily flows through the first inner segment. The flow of current through the electrical impedance of the tissue and the fluids of the first inner segment generates a voltage that is sensed by the first sensing electrode 11' and the second sensing electrode 12' and that is provided as an input to the bioimpedance measuring device 5 between the first voltage sensing input 511 and the second voltage sensing input 512 (the first voltage sensing pairs VS1). The bioimpedance measuring device 5 receives the sensed voltage from the pair of first sensing electrode 11 and second sensing electrode 12, amplifies the sensed voltage and filters out the high frequency components to provide a digitized basal impedance of the first inner body segment Zoa to output 53 and the change in the basal impedance of the first inner body segment dz to output 54.

The flow of current through the tissues and fluids of the first outer segment also necessarily flows through the second inner segment. The flow of current through the electrical impedance of the tissue and the fluids of the second inner segment generates a voltage that is sensed by the third sensing electrode 21 and fourth sensing electrode 22 and that is provided as an input to the bioimpedance measuring device 5 between the third voltage sensing input 521 and the fourth voltage sensing input 522 (the second voltage sensing pair VS2). The bioimpedance measuring device 5 receives the sensed voltage from third sensing electrode 21 and fourth sensing electrode 22, amplifies the sensed voltage and filters out the high frequency components to provide a digitized basal impedance of second inner body segment Zo2 to output 55 and the change in the basal impedance of the second inner body segment dz to output 56.

The measurements are performed to both calves either in turns or simultaneously with the same current. The initial impedance is measured before the pressure is applied to the cuffs 91 and 92. After applying the pressures to the cuffs there is much more blood in the tissues in the inner body segment between the cuffs 91 and 92. As a result of this the voltage sensed by electrodes (and the impedance) decreases. The speed of decreasing depends on how quickly the tissues are filling with blood. The lowest impedance is called the final impedance.

The bioimpedance measuring device generates outputs used as inputs to the computational circuitry as described earlier (referring to FIG. 1). The initial and final impedances Z1 and Z2 are compared to each other as a part of analysis. Using the arterial or venous blood flow occlusion, the measured signals can be analyzed as venous occlusion plethysmograms. For example the arterial flow into the leg is directly related to the decreasing speed of final impedance and a venous capacitance is characterized by the difference between the initial and final impedance.

It is obvious to a person skilled in the art that the apparatus of the present invention can be used for measuring a variability of other physiological signals. For example, different physiological signals can be used as a measure of autonomic nervous system function. Measurements can be classified as time domain analysis and frequency domain analysis. Time domain analysis is a general measure of autonomic nervous system balance and is based on altered versions of the measurement of the standard deviation of heart period, defined in terms of the sinus R—R intervals over time. There are six commonly used time domain measurements: SDANN, 24-hr SD, SD, RMSSD, RR50, and % RR50. Frequency domain analysis uses either autoregressive or fast Fourier transform techniques to delineate parasympathetic (high-frequency components) from sympathetic (low-frequency components) of autonomic control.

While the above is a description of the invention in its preferred embodiments, various modifications, alternate constructions and equivalents may be employed, only some of which have been described above. Therefore, the above description and illustration should not be taken as limiting the scope of the invention which is defined by the appended claims.

What is claimed is:

1. An apparatus for a simultaneous/synchronized noninvasive measurement of cardiorespiratory and related parameters comprising a bioimpedance measuring means (5) connectable to the body of the patient for injecting a current to a first outer body segment and sensing the voltage in the first and second inner body segments for generating output signals (53, 54, 55, 56, 57), characterized in that the apparatus further comprises a pressure sensing means (6) for the measurement of blood pressure, said sensing means being connected to the bioimpedance measuring means (5) for generating a blood pressure output signal, a respiratory flow sensor (7) for measuring the patient's respiration continuously, said respiratory flow sensor being connected to the bioimpedance measuring means (5) for generating a respiratory flow output signal, and a calculating means (83) for calculating cardiorespiratory and related parameters using said output signals.

2. The apparatus of claim 1, characterized in that the bioimpedance measuring means comprises a current source having a high-frequency current output;

means (31, 32) for injecting the output of said current source into the first outer segment of the patient to cause current flow in said first and second inner segments;

first sensing means (11, 12, 11', 12') for sensing a voltage caused by said current flow through the first inner segment of the patient, said voltage having a magnitude that varies in accordance with changes in electrical impedance of first outer body segment caused by the flow of blood in the first and second body segment during each cardiac cycle;

second sensing means (21, 22) for sensing a voltage caused by said current flow through the second inner segment of the patient, said voltage having a magnitude that varies in accordance with changes in electrical impedance of first outer body segment caused by the flow of blood in the second body segment during each cardiac cycle; and an electronic circuit connected to said first and second sensing means, said electronic circuit receiving said voltage sensed by said sensing means and generating output signals having a magnitude that changes in accordance with the flow of blood in the first segment during each cardiac cycle.

3. The apparatus of claim 1, characterized in that said calculating means further comprises a computational circuit block (83) that is responsive to said output signals from said bioimpedance measuring means.

4. The apparatus of claim 1, characterized in that the apparatus further comprises input means (81) connected to said computational circuit block for providing data thereto.

5. The apparatus of claim 1, characterized in that the apparatus further comprises a display device (85) connected to said calculating means (83), said display device displaying the calculated data.

6. A method for continuously, simultaneously/synchronously noninvasively measuring cardiorespiratory and related parameters in a patient by electrically connecting a bioimpedance device to the distal parts of the arms and legs of a patient through a first set of electrodes comprising at least one current injecting electrode for a leg and one for an arm and at least one voltage sensing electrode for a leg and one for an arm, injecting a first high-frequency constant alternating current via the current injecting electrode(s) and sensing the pulsatile voltage variations in the whole body generated by the electrical impedance of the tissues and the fluids in the whole body and obtaining electrocardiographic signals (ECG) from the heart and, alternating with said first current, injecting high-frequency constant alternating currents of predetermined different fixed frequencies via said current injecting electrode(s) and sensing different voltages caused by the different high-frequency currents in the body, and electrically connecting the bioimpedance device to different body segments of the patient through a second set of electrodes comprising at least one pair of sensing electrodes for sensing the pulsatile voltage changes in said segments caused by said first injected current in body segments, characterized in that the method further comprises the steps of electrically connecting a pressure sensor to a suitable location on the patient for measuring the blood pressure, electrically connecting a respiratory flow sensor to the patient's mouth/nose for measuring the patient's respiration continuously, and thereafter amplifying and digitizing the voltages sensed by said first sensing electrodes, the voltage changes sensed by said second sensing electrodes and the signals obtained from the pressure sensor and the respiratory flow sensor, transmitting the digitized data to a computational circuit block for calculating the desired cardiorespiratory and related parameters, and displaying the calculated data on a display with the on-line processed measurement results.

7. A method of claim 6, characterized in that the method further comprises a step of performing a conventional plethysmographic measurement in the extremities of the patient.

8. A method of claim 6, characterized in that the cardiorespiratory and related parameters to be calculated are the stroke volume, the stroke index, the heart rate, the cardiac output, the pulse wave velocity, the arterial compliance, stroke volume distribution index, the breathing frequency and amplitude, and the body water compartments and optionally, where the blood pressure sensor is used calculating the systolic arterial pressure, the diastolic arterial pressure, the mean arterial pressure, the systemic vascular resistance index, the left cardiac work, the left cardiac work index, and the arterial compliance.

9. A method of claim 7, characterized in that the cardiorespiratory and related parameters to be calculated are the stroke volume, the stroke index, the heart rate, the cardiac output, the pulse wave velocity, the arterial compliance, stroke volume distribution index, the breathing frequency and amplitude, and the body water compartments and optionally, where the blood pressure sensor is used calculating the systolic arterial pressure, the diastolic arterial pressure, the mean arterial pressure, the systemic vascular resistance index, the left cardiac work, the left cardiac work index and the arterial compliance.

* * * * *